United States Patent
Allier (10) Patent No.: US 10,400,208 B2
(45) Date of Patent: Sep. 3, 2019

(54) CELL-SORTING METHOD AND ASSOCIATED DEVICE

(71) Applicant: COMMISSARIAT A L'ENERGIE ATOMIQUE ET AUX ENERGIES ALTERNATIVES, Paris (FR)

(72) Inventor: Cedric Allier, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 575 days.

(21) Appl. No.: 14/907,260

(22) PCT Filed: Jul. 21, 2014

(86) PCT No.: PCT/EP2014/065636
§ 371 (c)(1),
(2) Date: Jan. 22, 2016

(87) PCT Pub. No.: WO2015/011096
PCT Pub. Date: Jan. 29, 2015

(65) Prior Publication Data
US 2016/0160174 A1 Jun. 9, 2016

(30) Foreign Application Priority Data
Jul. 23, 2013 (FR) .................... 13 57240

(51) Int. Cl.
*C12M 1/00* (2006.01)
*G01N 15/14* (2006.01)
(Continued)

(52) U.S. Cl.
CPC ............ *C12M 47/04* (2013.01); *C12M 23/22* (2013.01); *C12M 31/00* (2013.01);
(Continued)

(58) Field of Classification Search
None
See application file for complete search history.

(56) References Cited

U.S. PATENT DOCUMENTS 6,905,838 B1 * 6/2005 Bittner ................... G01N 21/21
435/173.1
2004/0229349 A1 * 11/2004 Daridon ............ B01L 3/502761
435/305.2
(Continued)

FOREIGN PATENT DOCUMENTS

JP 2012-530255 11/2012
WO 2012/062805 5/2012

OTHER PUBLICATIONS

International Search Report dated Sep. 10, 2014 in PCT/EP14/65636 filed Jul. 21, 2014.
(Continued)

*Primary Examiner* — Jill A Warden
*Assistant Examiner* — Brittany I Fisher
(74) *Attorney, Agent, or Firm* — Oblon, McClelland, Maier & Neustadt, L.L.P.

(57) ABSTRACT

A method of discriminating a living cell from a dead cell, and a device for implementing the method, the method including: using a lens-free imaging device to acquire a diffraction figure corresponding to a cell; and determining a light intensity on a central area of an elementary diffraction figure associated with the cell. It can thus be determined if the studied cell is a living cell or a dead cell.

12 Claims, 4 Drawing Sheets

(51) Int. Cl.
*G01N 21/47* (2006.01)
*G01N 15/10* (2006.01)
*G01N 21/85* (2006.01)
*G01N 33/483* (2006.01)
*G03H 1/04* (2006.01)
*G01N 21/45* (2006.01)
*G03H 1/00* (2006.01)
*G01N 21/03* (2006.01)

(52) U.S. Cl.
CPC ....... *G01N 15/1463* (2013.01); *G01N 21/453* (2013.01); *G01N 21/4788* (2013.01); *G01N 33/4833* (2013.01); *G03H 1/0005* (2013.01); *G03H 1/0443* (2013.01); *G03H 1/0465* (2013.01); *G01N 15/1436* (2013.01); *G01N 21/8507* (2013.01); *G01N 2015/1006* (2013.01); *G01N 2015/1454* (2013.01); *G01N 2021/036* (2013.01); *G03H 2001/0033* (2013.01); *G03H 2001/0447* (2013.01); *G03H 2222/34* (2013.01)

(56) References Cited

U.S. PATENT DOCUMENTS

| | | | | |
|---|---|---|---|---|
| 2005/0112541 | A1* | 5/2005 | Durack | C12N 5/0612 435/2 |
| 2009/0029870 | A1* | 1/2009 | Ward | G01N 15/1404 506/9 |
| 2009/0032449 | A1* | 2/2009 | Mueth | G02B 21/32 210/94 |
| 2011/0204256 | A1* | 8/2011 | Patt | G01N 15/14 250/458.1 |
| 2011/0223587 | A1* | 9/2011 | Schulman | G01N 15/1459 435/6.1 |
| 2012/0122084 | A1* | 5/2012 | Wagner | C12N 5/0612 435/6.1 |
| 2012/0225475 | A1* | 9/2012 | Wagner | G01N 15/14 435/288.7 |
| 2012/0288920 | A1* | 11/2012 | Takeda | B01L 3/502761 435/286.5 |
| 2013/0308135 | A1 | 11/2013 | Dubois et al. | |

OTHER PUBLICATIONS

French Search Report dated Jan. 13, 2014 in FR 1357240 filed Jul. 23, 2013.

Ryle, et al., "Multispectral lensless digital in-line holographic microscope: LED illumination," Proceedings of SPIE, vol. 7717, 2010, 8 pages.

Su, et al., "High-Throughput Lensfree Imaging and Characterization of a Heterogeneous Cell Solution on a Chip," Biotechnology and Bioengineering, vol. 102, No. 3, XP002584870, Feb. 2009, pp. 856-868.

Office Action dated May 29, 2018, in Japanese Patent Application No. 2016-528484 (w/English-language translation).

Geonsoo Jin, et al., "Lens-free shadow image based high-throughput continuous cell monitoring technique", Biosensors and Bioelectronics, 38 (2012) pp. 126-131.

* cited by examiner

CELL-SORTING METHOD AND ASSOCIATED DEVICE

TECHNICAL DOMAIN

This invention relates to the domain of methods of discriminating a living cell from a dead cell.

The invention also relates to a device for implementing such a method.

STATE OF PRIOR ART

Prior art includes different methods for discriminating a living cell from a dead cell, in other words a viable cell from a non-viable cell.

For example, there are fluorescence microscopy methods. These methods use an optical microscope to display a sample, and a fluorescent marker that preferentially fixes on one of the two categories of cell (living cells and dead cells). The fluorescent marker absorbs incident radiation at a first wavelength, and emits fluorescence radiation at a second wavelength in response. <<Marked cells>> are cells on which the fluorescent marker fixes. It is found that by illuminating a sample of marked cells with a radiation at the first wavelength, a living cell can be discriminated from a dead cell by identifying cells that emit fluorescence radiation at the second wavelength. In practice, cells with a colour corresponding to the wavelength of the fluorescence radiation, and cells that do not have this colour, are observed with the microscope.

For example, living cells can be marked using AM calcein as a fluorescent marker that fixes only to the living cells. Propidium iodide that only fixes to dead cells can also be used.

One disadvantage of these methods is that they are invasive; the cell sample is disturbed by the addition of the fluorescent marker.

Another disadvantage of these methods is that they are expensive; the fluorescence microscope must have excellent optical performances based on the use of high quality optical components. Furthermore, their field is limited, often smaller than 1 mm$^2$, which prevents simultaneous observation of a large number of cells.

One purpose of this invention is to disclose a method to discriminate a living cell from a dead cell that does not have at least one of the disadvantages of prior art.

In particular, one purpose of this invention is to disclose an economic method, particularly suitable for simultaneous observation of a large number of cells, for example several hundred and even several thousand cells.

It is also desirable to propose a non-invasive method that does not require the addition of a marking substance.

PRESENTATION OF THE INVENTION

This invention is defined by a method of discriminating a living cell from a dead cell in which:
  a light source is used to illuminate a sample of a liquid solution containing the cells; and
  a matrix photodetector is arranged facing the light source and acquires a global diffraction figure of the sample, the global diffraction figure comprising a plurality of elementary diffraction figures, each associated with a cell.

According to the invention, a cell is classified as being in the living cells or dead cells category, depending on a light intensity on a central area of an elementary diffraction figure associated with said cell.

Each elementary diffraction figure advantageously has a sequence of concentric closed curves.

Preferably, said central area is inscribed in an area delimited by a smallest diffraction ring of the elementary diffraction figure.

The method according to the invention may include the following steps:
  a value of a numeric indicator representative of the light intensity in said central area is determined;
  the value of the numeric indicator is compared with a predetermined threshold value; and
  depending on the result of this comparison, said cell is classified in one of the two categories: living cell or dead cell.

Advantageously, the numeric indicator is a maximum intensity or a mean intensity or a peak-to-peak intensity value.

The predetermined threshold value is preferably a reference intensity, and:
  a numeric indicator value lower than said reference intensity corresponds to a living cell; and
  a numeric indicator value higher than said reference intensity corresponds to a dead cell.

The method according to the invention is advantageously used to perform in situ monitoring of a cell treatment in a bioreactor.

The sample can be illuminated using a spatially coherent light source.

Advantageously, the global diffraction figure of the sample is acquired using a matrix photodetector placed facing the light source, no magnification device being placed between the sample and said matrix photodetector.

The invention also relates to a device for discriminating a living cell from a dead cell comprising:
  a light source, arranged to illuminate a sample of a liquid solution comprising cells; and
  a matrix photodetector placed facing the light source, arranged to acquire a global diffraction figure of the sample, the global diffraction figure comprising several elementary diffraction figures, each of which is associated with a cell.

According to the invention, the device comprises calculation means:
  receiving the global diffraction figure as input;
  determining the light intensity on a central area of an elementary diffraction figure associated with a cell; and
  providing as output a classification of said cell in one from the two categories: living cell or dead cell.

Each elementary diffraction figure advantageously includes a sequence of closed concentric curves.

Preferably, no magnification device is placed between the sample and the matrix photodetector.

The device according to the invention may include:
  a first sealed housing that holds the light source and has a first transparent window between the light source and the matrix photodetector;
  a second sealed housing that holds the matrix photodetector, and has a second transparent window between the first transparent window and the matrix photodetector;
the distance between the first transparent window and the second transparent window being variable, the first sealed housing, the light source, the second sealed housing and the matrix photodetector together forming an immersible probe.

According to a first embodiment of the invention, the distance between the first transparent window and the second transparent window is variable in time, the first transparent window and the second transparent window defining two planes parallel to each other, and the device according to the invention comprising means of displacing the second transparent window relative to the first transparent window.

The means for displacing the second transparent window relative to the first transparent window may include a rack driven in translation by a gear, and fixed relative to the second sealed housing.

According to a second embodiment of the invention, the distance between the first transparent window and the second transparent window is variable in space.

The first transparent window and the second transparent window may define two planes inclined relative to each other, such that the distance between the first transparent window and the second transparent window depends on the location on the second transparent window.

Advantageously, the light source is spatially coherent.

The calculation means can determine the light intensity on a central area of an elementary diffraction figure associated with a cell, the central area being inscribed in an area delimited by a smallest diffraction ring in the elementary diffraction figure.

The invention also relates to an immersible probe comprising:
  a light source, arranged to illuminate a sample of a liquid solution comprising particles; and
  a matrix photodetector positioned facing the light source, arranged to acquire a global diffraction figure of the sample, the global diffraction figure comprising several elementary diffraction figures each associated with a particle.

According to the invention, the immersible probe comprises:
  a first sealed housing, holding the light source and having a first transparent window between the light source and the matrix photodetector;
  a second sealed housing, holding the matrix photodetector, and having a second transparent window between the first transparent window and the matrix photodetector;
and the distance between the first transparent window and the second transparent window is variable.

According to a first embodiment of the immersible source according to the invention, the distance between the first transparent window and the second transparent window is variable in time, the first transparent window and the second transparent window defining two planes parallel to each other, and the immersible probe comprises means of displacing the second transparent window relative to the first transparent window.

Advantageously, the means for displacing the second transparent window relative to the first transparent window include a rack driven in translation by a gear, and fixed relative to the second sealed housing.

According to a second embodiment of the immersible source according to the invention, the distance between the first transparent window and the second transparent window is variable in space.

The first transparent window and the second transparent window may define two planes inclined relative to each other such that the distance between the first transparent window and the second transparent window depends on the location on the second transparent window.

The light source is advantageously spatially coherent.

The invention also relates to a bioreactor comprising a tank to hold a liquid solution comprising particles such as cells. The bioreactor comprises an immersible probe according to the invention, immersed in the liquid solution such that the space between the first transparent window and the second transparent window is occupied by said liquid solution.

The invention also relates to a method of using an immersible probe according to the invention.

According to this method:
  the immersible probe is immersed in a liquid solution comprising particles such as cells, said liquid solution occupying the space between the first transparent window and the second transparent window; and
  a distance between the first transparent window and the second transparent window is defined as a function of the particle concentration in the liquid solution and such that at least 30%, or even 50% or 80% of the elementary diffraction figures in a global diffraction figure are not superposed with another elementary diffraction figure, each elementary diffraction figure being associated with a particle such as a cell.

Advantageously, an immersible probe according to the first embodiment of the invention is used and the distance between the first transparent window and the second transparent window is defined by displacing the first transparent window relative to the second transparent window.

As a variant, an immersible probe according to the second embodiment of the invention is used and the distance between the first transparent window and the second transparent window is defined by defining a portion of the matrix photodetector used to obtain the global diffraction figure.

BRIEF DESCRIPTION OF THE DRAWINGS

This invention will be better understood after reading the description of example embodiments given purely for information and in no way limitative with reference to the appended drawings among which.

DETAILED PRESENTATION OF PARTICULAR EMBODIMENTS

Figure 1:
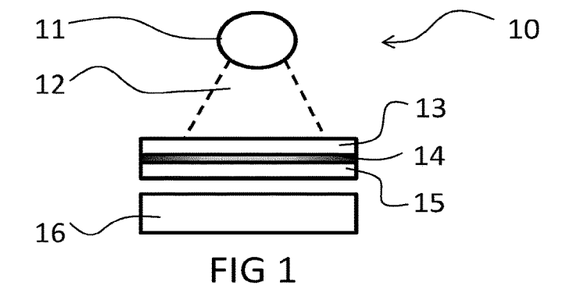
FIG. 1 illustrates a known lens-free imaging device.

We will firstly describe a lens-free imaging device 10 with reference to FIG. 1. Such a device is known to those skilled in the art, and an expert will easily find details of how to make such a device in the literature.

A light source 11 emits a light beam 12 illuminating a sample 14. The light source is preferably spatially coherent. The light source may be a laser diode, or a light emitting diode (LED) followed by a filter hole. The filter hole improves the spatial coherence of the light beam emitted by the LED. Advantageously, the light source is also temporally coherent.

For example, a LED may be used with an emission spectrum centred on 450 nm, namely an emission in the blue. The width of the peak at 450 nm is 40 nm. The emission power of the LED may for example be between 100 mW and 1 W. The LED is followed by a 150 μm diameter filter hole placed directly in contact with the LED.

The sample 14 is placed between the light source 11 and a matrix photodetector 16.

In the example shown in FIG. 1, the sample 14 is a liquid sample placed between two slides 13, 15 transparent at the emission wavelength of the light source. Therefore the device 10 according to the invention works in transmission. The distance between the slide 13 (on the same side as the light source) and the light source is usually between 1 cm and 10 cm.

For example, the sample 14 may be a sample of a biological liquid such as blood, a cell culture solution, a sample taken from nature such as a sample of water in a lake, etc. The device 10 can detect small diameter particles contained in the sample, typically with diameters between 100 nm and 500 μm.

The matrix photodetector 16 converts incident electromagnetic radiation into an analogue electrical signal. This matrix photodetector 16 is usually connected to an analogue-digital converter so as to provide a digital image. The term "matrix photodetector" is used because the detection area of a photodetector is composed of pixels forming a matrix. The matrix photodetector 16 may for example be a CCD (Charge-Coupled Device) sensor or a CMOS (Complementary Metal Oxide Semiconductor) sensor. Each pixel in the photodetector may for example be a square with a side smaller than 9 μm, and even smaller than 5 μm, for example 2.2 μm. In particular, a 24 mm$^2$ CMOS sensor with a pixel pitch equal to 2.2 μm can be used.

The matrix photodetector 16 detects a diffraction figure corresponding to the influence of particles in the sample 14 on the light beam 12. In particular, the matrix photodetector 16 detects a diffraction figure corresponding to interference between an incident light wave originating directly from the light source 11 and a light wave diffracted by particles in the sample 14. Such a diffraction figure is referred to as a <<hologram>>. One advantage of such a diffraction figure is that the detected signal is a large amplitude signal, due to the contribution of the signal originating directly from the light source. Another advantage of this diffraction figure is that the detected field of vision is large, for example more than 20 mm$^2$. The photodetector 16 is located close to the sample 14, for example at 0.8 mm from the slide 15 (slide on the same side as the photodetector 16).

Therefore, a diffraction figure corresponding to an object is detected, rather than the image of this object directly. This technique is called <<lens-free imaging>>. Throughout the text, the term <<lens-free imaging device>> is used to denote a device of this type, to detect a diffraction figure corresponding to an object. It should be noted that such a device may include a matrix of micro-lenses that focus the beam corresponding to interference to be detected onto each pixel. However, such a device does not include any magnification optics located between the object and the photodetector.

Those skilled in the art will easily be capable of positioning each of the elements relative to each other, including the light source 11, the sample 14 and the photodetector 16.

A support (not shown) could be provided to hold the sample 14, this support being located between the light source 11 and the photodetector 16.

According to the invention, this device 10 is used with a sample 14 of a liquid solution comprising cells. For example, a solution of HeLa cancer cells can be used. In particular, it will be chosen to use a 3-d sample: the thickness between the two slides 13, 15 may for example be 0.2 mm. The volume of the sample 14, imaged on the photodetector 16 in the form of a diffraction figure, is about 5 μL.

As a result, a global diffraction figure is acquired on the photodetector 16 corresponding to the interferences between waves originating directly from the light source 11 and waves emitted by the light source and then diffracted by the cells in the sample 14. The global diffraction figure comprises several elementary diffraction figures. Each elementary diffraction figure is associated with a cell in the sample 14, and corresponds to the interferences between waves originating directly from the light source 11 and waves emitted by the light source and then diffracted by said cell.

It can be seen that each elementary diffraction figure has a characteristic profile depending on whether the cell is living or dead.

Figure 2A:
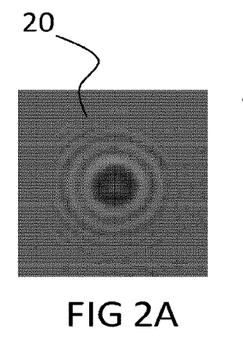
FIGS. 2A and 2B illustrate a diffraction figure obtained using the device in FIG. 1 for a living cell.

FIG. 2A illustrates an elementary diffraction FIG. 20 associated with a living HeLa cell. The elementary diffraction FIG. 20 is obtained using the device described above. In FIG. 2A, the abscissa axis and the ordinate axis together form the plane of the photodetector 16. Dark colours correspond to zones with low light intensity, and light colours correspond to zones with high light intensity. An alternation of dark and light rings called "diffraction rings" can be seen in FIG. 2A. These diffraction rings translate the circular profile of the observed cells. The elementary diffraction FIG. 20 has an axial symmetry about an axis of symmetry passing through the common centre of the dark and light rings.

Figure 2B:
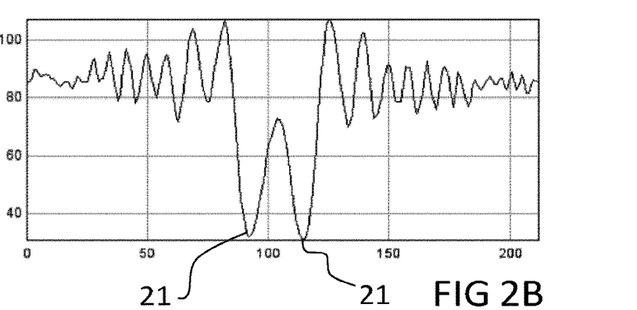

FIG. 2B illustrates a section through this elementary diffraction FIG. 20, in a plane passing through said axis of symmetry. In FIG. 2B, the abscissa axis corresponds to a distance graduated in pixels. The ordinate axis corresponds to a light intensity graduated in shades of grey (from 0 to 255, namely 256 shades of grey for an analogue signal at the output from the photodetector 16 converted into a digital signal coded on 8 bits). A low value of the grey shade corresponds to a low light intensity. A high value of the grey shade corresponds to a high light intensity. The axis of symmetry of the elementary diffraction FIG. 20 can be seen in FIG. 2B, this axis being defined by a straight line with abscissa equal to 105 pixels. A central peak can be distinguished on this axis for which the maximum grey shade is equal to about 70, surrounded by two secondary peaks with grey shades equal to about 110. This central peak with low light intensity can be seen in FIG. 2A, on which it can be seen that the rings are centred on a grey disk.

Figure 3A:
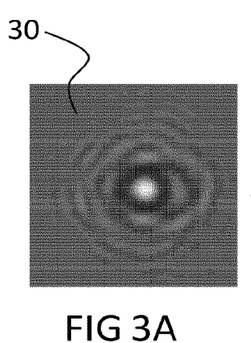
FIGS. 3A and 3B illustrate a diffraction figure obtained using the device in FIG. 1 for a dead cell.

FIG. 3A illustrates an elementary diffraction FIG. 30 associated with a dead HeLa cell. The elementary diffraction figure is obtained using the device described above. Once again, an alternation of dark and light rings can be seen. The elementary diffraction FIG. 30 has an axial symmetry about an axis of symmetry passing through the common centre of dark and light rings.

Figure 3B:
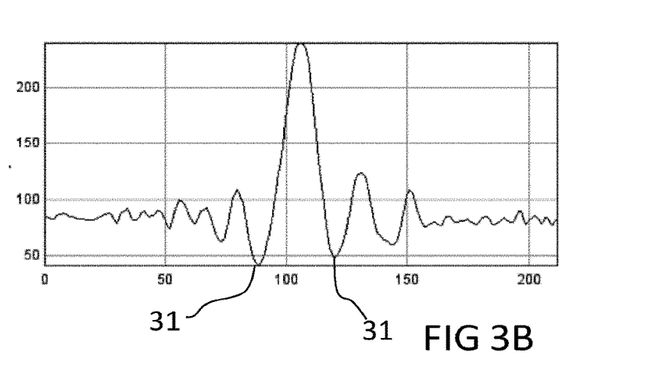

FIG. 3B illustrates a section through this elementary diffraction FIG. 30, in a plane passing through said axis of symmetry.

FIGS. 3A and 3B correspond to FIGS. 2A and 2B respectively, but this time in the case of a dead cell.

The axis of symmetry of the elementary diffraction FIG. 30 can be seen in FIG. 3B, this axis being defined by a straight line with abscissa equal to 105 pixels. A central peak can be distinguished on this axis, for which the grey shade is equal to about 250, surrounded by two secondary peaks with grey shades equal to about 110. This central peak with high light intensity can be seen in FIG. 3A, on which it can be seen that the rings are centred on a white disk.

The difference between the elementary diffraction FIG. 20 associated with a living cell and the elementary diffraction FIG. 30 associated with a dead cell is sufficiently significant so that the state of the cell can be detected from its diffraction figure. Therefore, this difference can be used to discriminate a living cell from a dead cell.

It can be seen that the two elementary diffraction figures are different particularly on a central zone, in this case in the form of a disk, defined on a diffraction figure. This disk is centred on the centre of the rings of said elementary diffraction figure. It is delimited by the first ring in an elementary diffraction figure. This first ring in this case corresponds to the minimum light intensity ring. The minimum and maximum intensities 21 and 31 corresponding to this first ring in the elementary diffraction figure can be seen in FIG. 2B and FIG. 3B respectively. The central disk may for example be a disk with a diameter less than 100 pixels.

It can be seen that a modification in the profile of a cell, for example if it becomes oval, results in a modification to the associated elementary diffraction figure. The associated elementary diffraction figure will always have a series of closed concentric curves, which will also be called <<diffraction rings>>. These closed curves surround an area delimited by a smallest elementary diffraction ring.

The basic idea of the invention consists of using a light intensity on a central area of an elementary diffraction figure, to classify a corresponding cell in the living cells category or in the dead cells category. This area is called the central area, because it is concentric with the diffraction rings. In particular, the central area is inscribed in an area delimited by a smallest diffraction ring. Such an area corresponds for example to the central disk as defined above.

Therefore, it can be seen that the invention provides a method of discriminating a living cell from a dead cell, that does not require addition of a marking substance.

The equipment means necessary to implement this method are simple and inexpensive; in particular, it is a lens-free imaging device. The imaging device does not require the use of expensive optics. The invention does not require the use of very powerful calculation means, because no attempt is made to reconstruct an image of cells from their elementary diffraction figures. Nor is any attempt made to process elementary diffraction figures to compare them with a library of reference diffraction figures. A cell is classified simply by using a light intensity on a predetermined area.

Furthermore, since no attempt is made to reconstruct a cell, there is no need to know the distance between the cell and the photodetector. Therefore, it is easy to analyse a population of cells contained in a volume, rather than simply in a plane.

Nor is there any need to focus on a particular plane, which makes it easy to analyse a population of cells contained in a volume.

Another advantage of the method according to the invention is its precision; a precise count of the numbers of living cells and dead cells in a given region can be made.

We will now more precisely illustrate the use of a light intensity on a central area of an elementary diffraction figure.

Figure 4A:
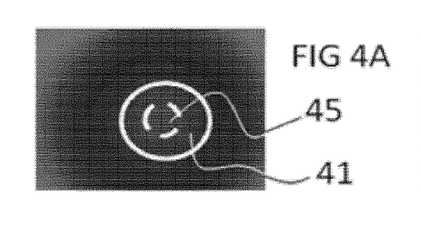
FIG. 4A illustrates a central disk of the diffraction figure shown in FIG. 2A.

FIG. 4A illustrates the central disk 41 as defined above, in the diffraction figure shown in FIG. 2A. It can be seen that this central disk is dark. It corresponds to low light intensities, which is characteristic of a living cell. The total diameter of the central disk 41 in this case is about 30 pixels. A central area 45 can be defined on the central disk 41, in this case a concentric disk with a diameter less than or equal to the diameter of the central disk 41.

Figure 4B:
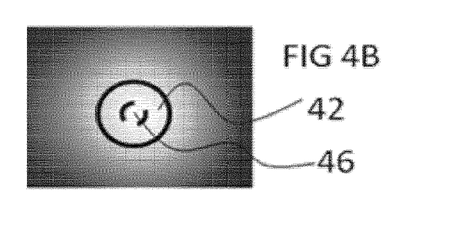
FIG. 4B illustrates a central disk of the diffraction figure shown in FIG. 3A.

FIG. 4B illustrates the central disk 42 as defined above, in the diffraction figure shown in FIG. 3A. It can be seen that this central disk is light. It corresponds to high light intensities, which is characteristic of a dead cell. A central area 46 can be defined on the central disk 42, in this case a concentric disk with a diameter less than or equal to the diameter of the central disk 42.

Therefore, it can be seen that it is sufficient to evaluate the light intensity on a central area inscribed in the central disk 41 or 42, to know whether or not a corresponding cell is living or dead.

A numeric indicator can be defined to characterise the light intensity in the central area 45 or 46. In the example shown in FIGS. 4C and 4D, this numeric indicator is the average value of the grey shade in the central area. Since in this case the elementary diffraction figure has axial symmetry, it is possible to work on a section of this diffraction figure passing through the axis of symmetry.

Figure 4C:
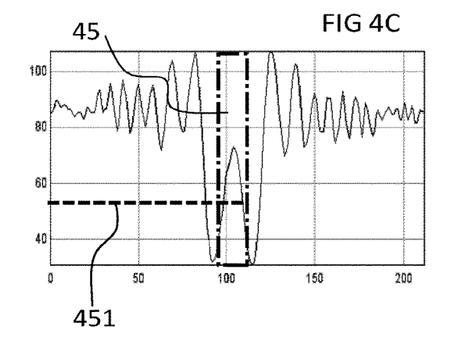
FIGS. 4C and 4D illustrate a numeric indicator according to the invention.

FIG. 4C corresponds to FIG. 2B, on which a central area 45 according to the invention has been identified. The numeric indicator is identified in FIG. 4C by the straight line 451 at ordinate 55.

Figure 4D:
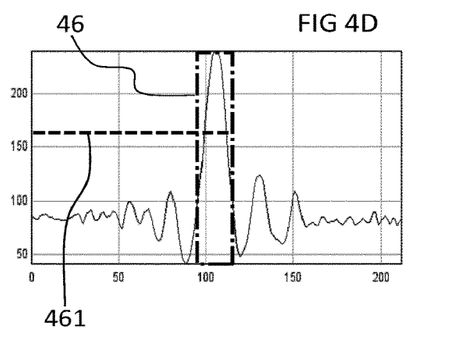

FIG. 4D corresponds to FIG. 3B, on which a central area 46 according to the invention has been identified. The numeric indicator is identified in FIG. 4D by the straight line with ordinate 160.

According to the invention, the value of this numeric indicator is used to classify a cell in the category of living cells or dead cells.

A predetermined threshold value is fixed to separate values of the numeric indicator associated with a living cell and values of the numeric indicator associated with a dead cell.

In this case, a reference intensity will be considered in particular:
  a numeric indicator lower than this reference intensity corresponds to a living cell; and
  a numeric indicator higher than this reference intensity corresponds to a dead cell.

The reference intensity, expressed as a grey shade, may for example be fixed between 80 and 150, typically 140.

Thus, all that is necessary to distinguish a living cell from a dead cell is to:
  calculate said numeric indicator; then
  compare the numeric indicator with a predetermined threshold value.

In particular, the threshold value may be established experimentally.

Different types of numeric indicators can be provided without going outside the scope of this invention. For example, an absolute light intensity or a peak-to-peak amplitude of the light intensity, etc., may be considered.

In this case, we considered the example of HeLa cells, but it would be possible to classify any type of cell in the same manner.

In the example shown in the figures, a living cell corresponds to a low light intensity at the centre of the elementary diffraction figure, while a dead cell corresponds to a high light intensity at the centre of the elementary diffraction figure. The characteristic profile of the elementary diffraction figure associated with a living cell or a dead cell may depend on the type of cell studied. Thus, it is possible that a low light intensity at the centre of the elementary diffraction figure corresponds to a dead cell and that a high light intensity at the centre of the elementary diffraction figure corresponds to a living cell.

The central area according to the invention may be an area with predetermined dimensions, for example a disk centred on the centre of the diffraction rings in the elementary diffraction figure, and with a predetermined diameter. The following steps can be performed to fix this predetermined diameter:

it is considered that the diffraction figure for a cell is an Airy pattern. The diameter of the smallest dark ring in the elementary diffraction figure is defined by the distance between the cell and the photodetector, and by an angle θ such that sin $$\theta = 1,22 \frac{\lambda}{d},$$

where λ is the emission wavelength of the light source, and d is the diameter of a cell. The diameter of the smallest dark ring defines the diameter of the central disk 41, 42. If the thickness of the sample, the wavelength of the light source and the order of magnitude of the cell diameter are known, an interval of values of the diameter of the central disk 41, 42 can be evaluated.

the lower value of this interval is selected;
the predetermined diameter of the central area is defined as being less than or equal to this lower value of interval.

As a variant, it will be possible to identify the smallest dark ring diameter on each elementary diffraction figure. The diameter of the central area may for example be equal to a fixed fraction of the diameter of the smallest dark ring.

The diameter of the central disk may for example be between 10 and 50 pixels (even between 20 and 50 pixels). The diameter of the central area may for example be between 5 and 50 pixels (even between 10 and 50 pixels).

Figure 5:
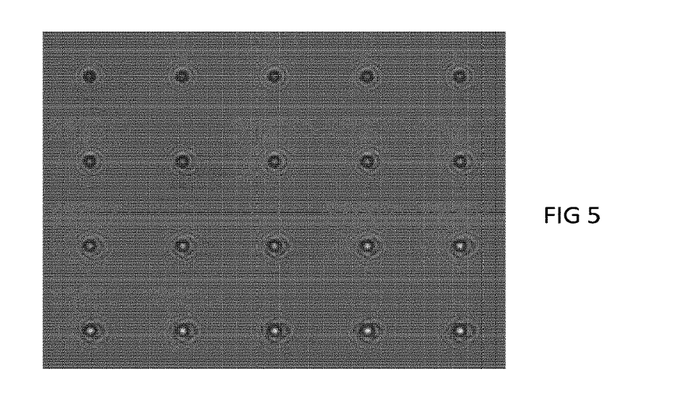
FIG. 5 illustrates the variation in the diffraction figure associated with a cell, when said initially living cell is progressively made non-viable until it dies.

FIG. 5 illustrates the variation of the elementary diffraction figure associated with a cell, when said cell initially living cell progressively deteriorates until it dies. The temperature of the initially living HeLa cell is increased from 37° C. to 45° C. in ten minutes. An elementary diffraction figure of the cell is recorded every 30 seconds. The elementary diffraction figures are stored in chronological order of their acquisitions, from left to right and from top to bottom. It can be seen that there is a progressive variation of the elementary diffraction figure from a figure like that shown in FIG. 2A towards a figure like that shown in FIG. 3A. This variation is monotonic; the central peak progressively becomes lighter. FIG. 5 clearly confirms that an intensity threshold can be defined on a central area according to the invention, to discriminate a living cell from a dead cell.

Figure 6:
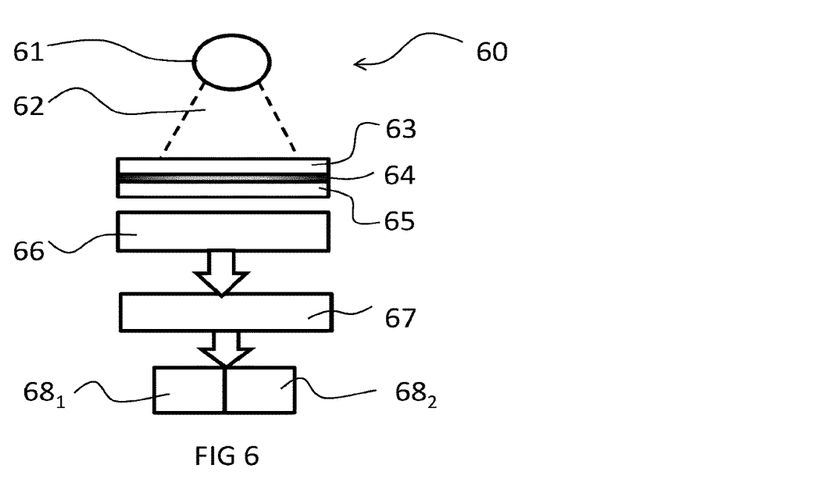
FIG. 6 diagrammatically illustrates a device to implement the method according to the invention.

FIG. 6 diagrammatically illustrates a device 60 to implement the method according to the invention. The numeric references 61, 62, 63, 64, 65, 66 in FIG. 6 correspond to numeric references 11, 12, 13, 14, 15 and 16 respectively in FIG. 1.

The light source 61 is arranged to illuminate a sample of a liquid solution containing cells.

The photodetector 66 is a matrix photodetector placed facing the light source and arranged to acquire a global diffraction figure of the sample, the global diffraction figure comprising several elementary diffraction figures each associated with a cell.

The photodetector 66 is connected to calculation means 67 that receive the global diffraction figure like that defined above, as input.

The calculation means determine the light intensity on a central area of an elementary diffraction figure associated with a cell, and provide a classification of said cell into either the living cell category 68$_1$ or the dead cell category 68$_2$, at the output. The central area is defined earlier, to illustrate the method according to the invention.

In particular, the calculation means are arranged to:
calculate the numeric indicator as defined above;
compare this numeric indicator with a predetermined threshold value;
assign the cell corresponding to said elementary diffraction figure, to one of the two categories 68$_1$ and 68$_2$.

In particular, the calculation means include electronic means and computer and/or software means. Typically, it comprises a digital or analogue electronic circuit, preferably dedicated, associated with a microprocessor and/or a computer.

The method according to the invention may advantageously be used for in situ control of a cell treatment in a bioreactor.

The method according to the invention uses elementary diffraction figures each associated with a cell. For each elementary diffraction figure to be useable, it is essential that the figures are not superposed on each other. Therefore, the concentration of cells in the sample 14 must be less than a predetermined maximum concentration, for a given thickness.

For example, in the embodiment described with reference to FIG. 1, it is only possible to image up to 10000 elementary diffraction figures on the photodetector 16, with an area of 24 mm$^2$. This corresponds to a maximum concentration of 2*10$^6$ cells/mL, the volume of the sample 14 being equal to approximately 5 µL.

Therefore, it can be seen that it may be necessary to adapt a lens-free imaging device used to implement the method according to the invention, to the concentration of cells in the sample 14.

An immersible probe is disclosed for this purpose, intended particularly to implement the method according to the invention. It could be envisaged to use this immersible probe for other purposes. This is why the immersible probe only will be described in the remainder of this disclosure, independently of the calculation means to implement steps of the method according to the invention.

The principle used in this immersible probe consists of adapting the thickness of the sample to its concentration in particles, in this case cells.

The immersible probe is adapted to measurements made by immersing the probe in a liquid solution. The result is that there is no need for a sampling step and deposition on a slide. Disturbances to the sample due to its observation are also limited because the sample is not isolated from the remainder of the liquid solution.

Figure 7:
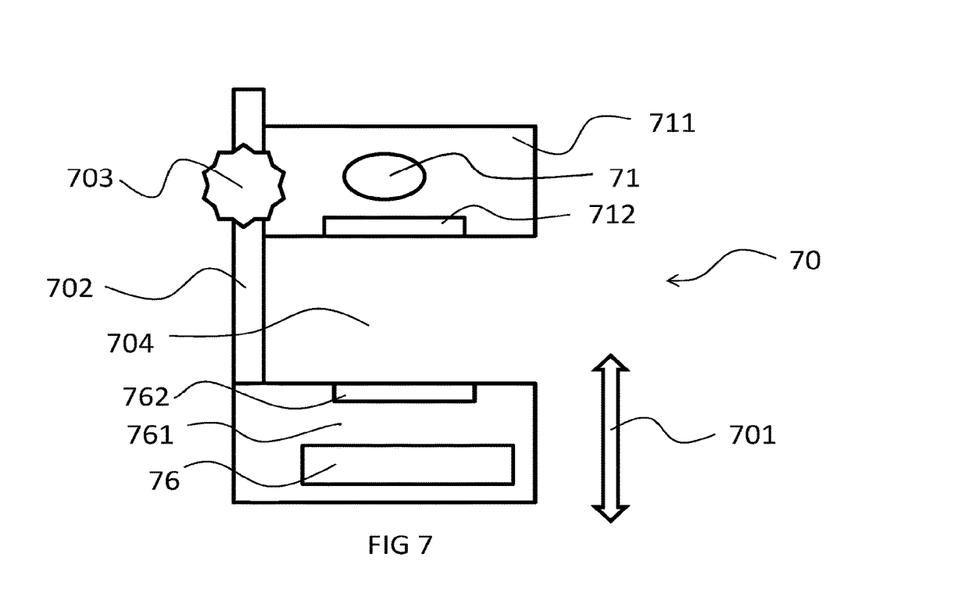
FIG. 7 diagrammatically illustrates a first embodiment of an immersible probe according to the invention.

FIG. 7 diagrammatically illustrates a first embodiment of the immersible probe 70 according to the invention.

References 71 and 76 in FIG. 7 correspond to references 11 and 16 in FIG. 1 respectively. Therefore the light source 71 and the photodetector 76 together form a lens-free imaging device as disclosed with reference to FIG. 1.

The immersible probe 70 comprises a first sealed housing 711 that holds the light source 71. Therefore the light source 71 is protected inside a sealed housing, so that this source can be fully immersed without any risk of damaging it. The first sealed housing 711 has a first window 712, transparent at the emission wavelength of the light source 71. The first window 712 is located between the light source 71 and the photodetector 76.

The immersible probe 70 also comprises a second sealed housing 761, holding the photodetector 76. Therefore, the photodetector 76 is protected inside a sealed housing, so that it can be fully immersed without any risk of damaging it. The photodetector is not simply covered it with a protective slide, but completely surrounded inside a casing. The second sealed housing 761 has a second window 762, transparent at the emission wavelength of the light source 71. The second window 762 is located between the first window 712 and the photodetector 76.

The sample is composed of a portion of the liquid solution in which the immersible probe 70 is fully immersed, this portion of liquid solution occupying the space 704 between the first transparent window 712 and the second transparent window 762. The liquid solution comprises particles such as cells.

The photodetector 76 is arranged to acquire a global diffraction figure comprising a plurality of elementary diffraction figures, each associated with a particle. It is required to adapt the thickness of the sample to its concentration in cells, such that at least 80% of the elementary diffraction figures in a global diffraction figure are not superposed with another elementary diffraction figure. To achieve this, the distance between the first transparent window 712 and the second transparent window 762 is variable.

In the embodiment shown in FIG. 7, this distance is variable in time.

The first transparent window 712 is parallel to the second transparent window 762. The second transparent window 762 is free to move along an axis 701 orthogonal to the plane of the first and second windows.

The second housing 761 is fixed relative to a rod 702 oriented along the axis 701. The rod 702 is notched. It forms a rack driven in translation by a gear (not shown). The gear is rotated by a knurled knob 703. Therefore the rod 702 driving the second housing 761 with it, can be translated along the axis 701 relative to the first housing 711.

Those skilled in the art could provide several variants to displace one transparent window relative to another transparent window along an axis orthogonal to the plane of these two windows, without going outside the scope of this invention.

The distance between the first transparent window 712 and the second transparent window 762 can thus be adjusted by displacing the second transparent window 762 relative to the first transparent window 712.

The immersible probe may be connected to calculation means (not shown) like that described above with reference to FIG. 6. In other words, the device 60 as shown in FIG. 6 may include an immersible probe according to the invention, the light source of the immersible source forming the light source 61 and the photodetector of the immersible probe forming the photodetector 66.

Figure 8:
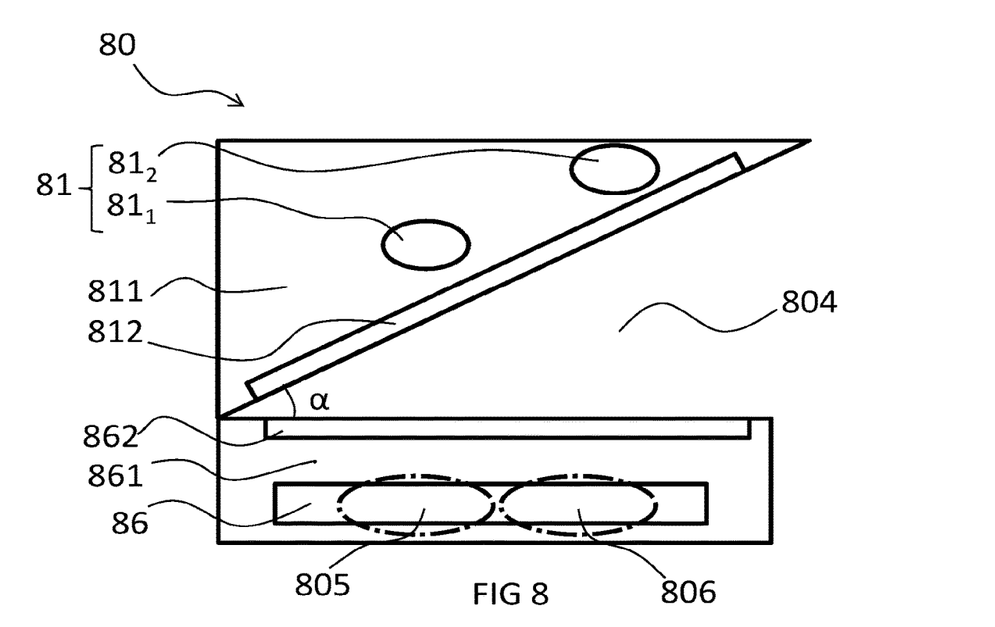
FIG. 8 diagrammatically illustrates a second embodiment of an immersible probe according to the invention.

FIG. 8 diagrammatically illustrates a second embodiment of an immersible probe 80 according to the invention.

Only the differences between the immersible probe 80 and the immersible probe 70 will be described. The numeric references 81, 811, 812, 86, 861, 862 and 804 in FIG. 8 correspond to numeric references 71, 711, 712, 76, 761, 762 and 704 respectively in FIG. 7.

In the embodiment shown in FIG. 8, the distance between the first transparent window 812 and the second transparent window 862 is variable in space.

The first transparent window 812 is inclined by an angle α relative to the second transparent window 862, these two windows being plane. The angle α is typically between 10° and 45°.

As a variant, it would be possible to provide a plane window, and a window with a stepped profile.

The light source 81 is composed of several unit light sources $81_1$, $81_2$ distributed above the first transparent window 812. This characteristic is not essential, and it could also be possible to use a light source composed of a single LED or laser diode, as disclosed with reference to FIG. 1.

An area 805 of the photodetector 86 corresponds to a small distance between the first transparent window 812 and the second transparent window 862. This area 805 is used to acquire a global diffraction figure when the concentration of the liquid solution is high, for example more than $10^6$ cells/mL. The area 805 is facing the unit light source $81_1$.

An area 806 of the photodetector 86 corresponds to a long distance between the first transparent window 812 and the second transparent window 862. This area 806 is used to acquire a global diffraction figure when the concentration of the liquid solution is low, for example between $10^4$ and $10^5$ cells/mL. The area 806 is located facing the unit light source $81_2$.

The distance between the first transparent window 812 and the second transparent window 862 can thus be adjusted, by defining a portion of the photodetector 86 used to obtain elementary diffraction figures to be analysed.

Figure 9:
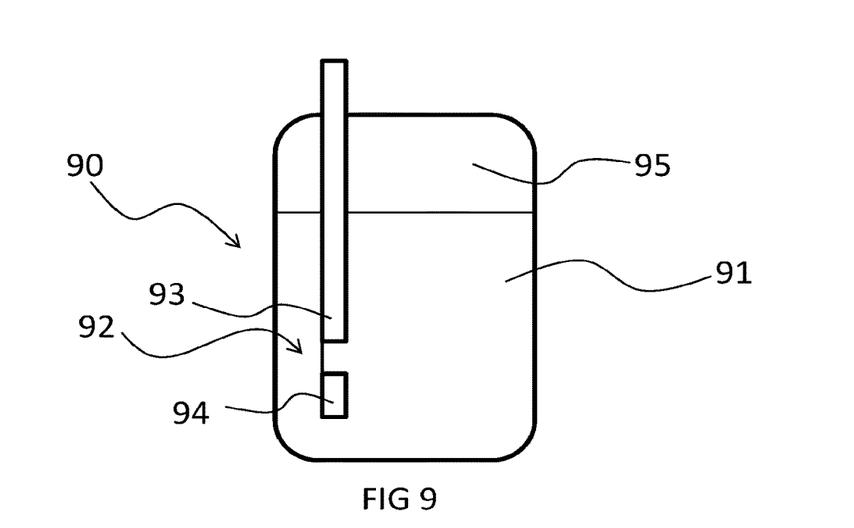
FIG. 9 diagrammatically illustrates a bioreactor according to the invention.

FIG. 9 diagrammatically illustrates a bioreactor 90 according to the invention. In this case, the bioreactor 90 denotes a device intended to cultivate cells or tissues in the context of a cell culture, or to implement a chemical process involving organisms or active biochemical substances derived from these organisms.

A bioreactor is designed to provide optimum conditions for a cell culture or a chemical process. This can be done by adjusting and controlling different parameters such as:
  the stirring of the liquid solution containing the cells, organisms or active biochemical substances;
  the pH of this solution;
  the temperature of this solution;
  the oxygen content dissolved in this solution.

In the example shown in FIG. 9, a liquid solution 91 comprising cells is added into the bioreactor 90. This solution is located in a tank 95 of the bioreactor.

Probes are inserted through openings formed in the bioreactor tank to check conditions inside the bioreactor 90. One of these openings is used to insert an immersible probe 92 according to the invention. The immersible probe 92 is in the form of an elongated cylinder with a diameter less than 12 mm and a length of more than 50 mm. The immersible probe 92 has an upper part 93 receiving the first sealed housing as described above, and a lower part 94 receiving the second sealed housing as described above. The space between these two housings is occupied by the liquid solution 91.

The variation with time of a content of living cells in the bioreactor can thus be measured. The acquisition time of a global diffraction figure is advantageously of the order of a millisecond, to avoid any influence of cell movements.

The invention claimed is:

1. A method of discriminating a living cell from a dead cell implemented using a lens-free imaging device including a light source and a matrix photodetector, the method comprising:
   using the light source to illuminate a sample of a liquid solution containing cells;
   arranging the matrix photodetector facing the light source, and acquiring a global diffraction figure of the sample, the global diffraction figure comprising a plurality of elementary diffraction figures each associated with a cell, each elementary diffraction figure having a succession of closed concentric curves; and
   classifying a cell in one of a living cells category or a dead cells category, depending on a light intensity on a central area of an elementary diffraction figure associated with the cell,
   wherein the central area is inscribed in an area delimited by a smallest diffraction ring of the elementary diffraction figure.

2. A method according to claim 1, further comprising:
   determining a value of a numeric indicator representative of the light intensity in the central area;
   comparing the value of the numeric indicator with a predetermined threshold value; and
   depending on a result of this comparison, classifying the cell in one of the living cells category or the dead cells category.

3. A method according to claim 2, wherein the numeric indicator is a maximum intensity or a mean intensity or a peak-to-peak intensity value.

4. A method according to claim 3, wherein the predetermined threshold value is a reference intensity, and:
   a numeric indicator value lower than the reference intensity corresponds to a living cell; and
   a numeric indicator value higher than the reference intensity corresponds to a dead cell.

5. A method according to claim 1, used to perform in situ monitoring of a cell treatment in a bioreactor.

6. A method of discriminating a living cell from a dead cell implemented using a lens-free imaging device including a light source and a matrix photodetector, the method comprising:
   using the light source to illuminate a sample of a liquid solution containing cells,
   arranging the matrix photodetector facing the light source, and acquiring a global diffraction figure of the sample, the global diffraction figure comprising a plurality of elementary diffraction figures each associated with a cell, each elementary diffraction figure having a succession of closed concentric curves; and
   classifying a cell in one of a living cells category or a dead cells category, depending on a light intensity on a central area of an elementary diffraction figure associated with the cell,
   wherein the global diffraction figure of the sample is acquired using a matrix photodetector placed facing the light source, no magnification device being placed between the sample and the matrix photodetector.

7. A device for discriminating a living cell from a dead cell comprising:
   a light source, arranged to illuminate a sample of a liquid solution comprising cells; and
   a matrix photodetector placed facing the light source, forming a lens-free imaging device with the light source, and arranged to acquire a global diffraction figure of the sample, the global diffraction figure comprising plural elementary diffraction figures each of which is associated with a cell, each elementary diffraction figure having a succession of closed concentric curves;
   a calculation means configured to:
   receive the global diffraction figure as an input;
   determine the light intensity on a central area of an elementary diffraction figure associated with a cell;
   provide as an output a classification of the cell as a living cell or a dead cell;
   wherein no magnification device is placed between the sample and the matrix photodetector;
   a first sealed housing, holding the light source and including a first transparent window between the light source and the matrix photodetector; and
   a second sealed housing, holding the matrix photodetector, and including a second transparent window between the first transparent window and the matrix photodetector;
   wherein a distance between the first transparent window and the second transparent window is variable;
   the first sealed housing, the light source, the second sealed housing, and the matrix photodetector together forming an immersible probe.

8. A device according to claim 7, wherein the distance between the first transparent window and the second transparent window is variable in time, the first transparent window and the second transparent window defining two planes parallel to each other, and the device further comprising means for displacing the second transparent window relative to the first transparent window.

9. A device according to claim 8, wherein the means for displacing the second transparent window relative to the first transparent window includes a rack driven in translation by a gear, and fixed relative to the second sealed housing.

10. A device according to claim 7, wherein the distance between the first transparent window and the second transparent window is variable in space.

11. A device according to claim 10, wherein the first transparent window and the second transparent window define two planes inclined relative to each other, such that the distance between the first transparent window and the second transparent window depends on a location on the second transparent window.

12. A device for discriminating a living cell from a dead cell comprising:
   a light source, arranged to illuminate a sample of a liquid solution comprising cells; and
   a matrix photodetector placed facing the light source, forming a lens-free imaging device with the light source, and arranged to acquire a global diffraction figure of the sample, the global diffraction figure comprising plural elementary diffraction figures each of which is associated with a cell, each elementary diffraction figure having a succession of closed concentric curves;
   a calculation means configured to:
   receive the global diffraction figure as an input;
   determine the light intensity on a central area of an elementary diffraction figure associated with a cell;
   provide as an output a classification of the cell as a living cell or a dead cell; and
   wherein no magnification device is placed between the sample and the matrix photodetector, and
   wherein the calculation means determines the light intensity on a central area of an elementary diffraction figure associated with a cell, the central area being inscribed in an area delimited by a smallest diffraction ring in the elementary diffraction figure.

* * * * *